US00PP18504P2

(12) United States Plant Patent
Strasko

(10) Patent No.: US PP18,504 P2
(45) Date of Patent: Feb. 19, 2008

(54) ***PENNISETUM* PLANT NAMED 'FIREWORKS'**

(50) Latin Name: *Pennisetum setaceum*
Varietal Denomination: Fireworks

(76) Inventor: Ronald Strasko, 17 W. Main St., Leola, PA (US) 17540

( * ) Notice: Subject to any disclaimer, the term of this patent is extended or adjusted under 35 U.S.C. 154(b) by 14 days.

(21) Appl. No.: 11/503,631

(22) Filed: Aug. 14, 2006

(51) Int. Cl.
*A01H 5/00* (2006.01)

(52) U.S. Cl. ..... Plt./384

(58) Field of Classification Search ..... Plt./384
See application file for complete search history.

*Primary Examiner*—Kent Bell
*Assistant Examiner*—June Hwu
(74) *Attorney, Agent, or Firm*—Penny J. Aguirre

(57) ABSTRACT

A new cultivar of *Pennisetum setaceum* named 'Fireworks', characterized by its unique variegated foliage comprised of vertical bands of burgundy, green, and white combined with a vigorous growth habit and showy pale red-purple plumes from early summer until frost.

2 Drawing Sheets

Botanical classification: *Pennisetum setaceum.*
Varietal denomination: 'Fireworks'.

BACKGROUND OF THE INVENTION

The present invention relates to a new and distinct cultivar of *Pennisetum setaceum* and will be referred to hereafter by its cultivar name, 'Fireworks'. 'Fireworks' represents a new cultivar of Purple fountain grass, a warm-season, ornamental grass grown for container and landscape use.

The inventor discovered and selected the new cultivar, 'Fireworks', as a culm sport of *Pennisetum setaceum* 'Rubrum' (not patented) in a container at his nursery in Leola, Pa. in spring of 2004.

The new cultivar 'Fireworks' was selected for the unique foliage coloration with leaf blades that are variegated with longitudinal stripes of white, green and burgundy that impart a candy cane-like appearance. The parent plant, *Pennisetum setaceum* 'Rubrum', has foliage that is non-variegated; burgundy in color when grown in full sun and green in color when grown in full shade. 'Fireworks' can also be compared to *Pennisetum setaceum* 'Cupreum' (not patented), which has green to red foliage and lacks leaf variegation.

Asexual reproduction of the new cultivar was first accomplished by culm division in Leola, Pa. in June of 2004 by the inventor. The characteristics of this cultivar have been determined to be stable and are reproduced true to type in successive generations via division and tissue culture.

SUMMARY OF THE INVENTION

The following traits have been repeatedly observed and represent the characteristics of the new cultivar. The new *Pennisetum* has not been observed under all possible environmental conditions. The phenotype may vary somewhat with variations in temperature, day-length, light intensity, soil types, and water and fertility levels without, however, any variance in genotype. The general observations, and descriptions that follow describe plants that were grown outdoors in Leola, Pa. for a period of one year. These attributes in combination distinguish 'Fireworks' from all other selections of *Pennisetum* known to the inventor.

1. The foliage of 'Fireworks' exhibits a longitudinal banding pattern of vertical bands of white, burgundy, and green. The parent plant has foliage that is non-variegated with foliage that is solid burgundy or green foliage dependent on light levels.
2. 'Fireworks' reaches a height of about 1.2 m (4 ft), and a spread of about 0.8 m, similar to the parent plant.
3. 'Fireworks' blooms in late June until frost in Pennsylvania with plumes that open red-purple color and turn light brown as they mature.
4. 'Fireworks' exhibits a vigorous growth habit.
5. 'Fireworks' is a grown as a tender perennial in climates colder than USDA Zone 9.

BRIEF DESCRIPTION OF THE DRAWING

The accompanying colored photographs illustrate the overall appearance and distinct characteristics of the new *Pennisetum* as grown for one year.

The photograph in FIG. 1 was taken in late summer and illustrates the overall habit and appearance of 'Fireworks' as grown outdoors in a trial plot in Leola, Pa.

Figure 1:
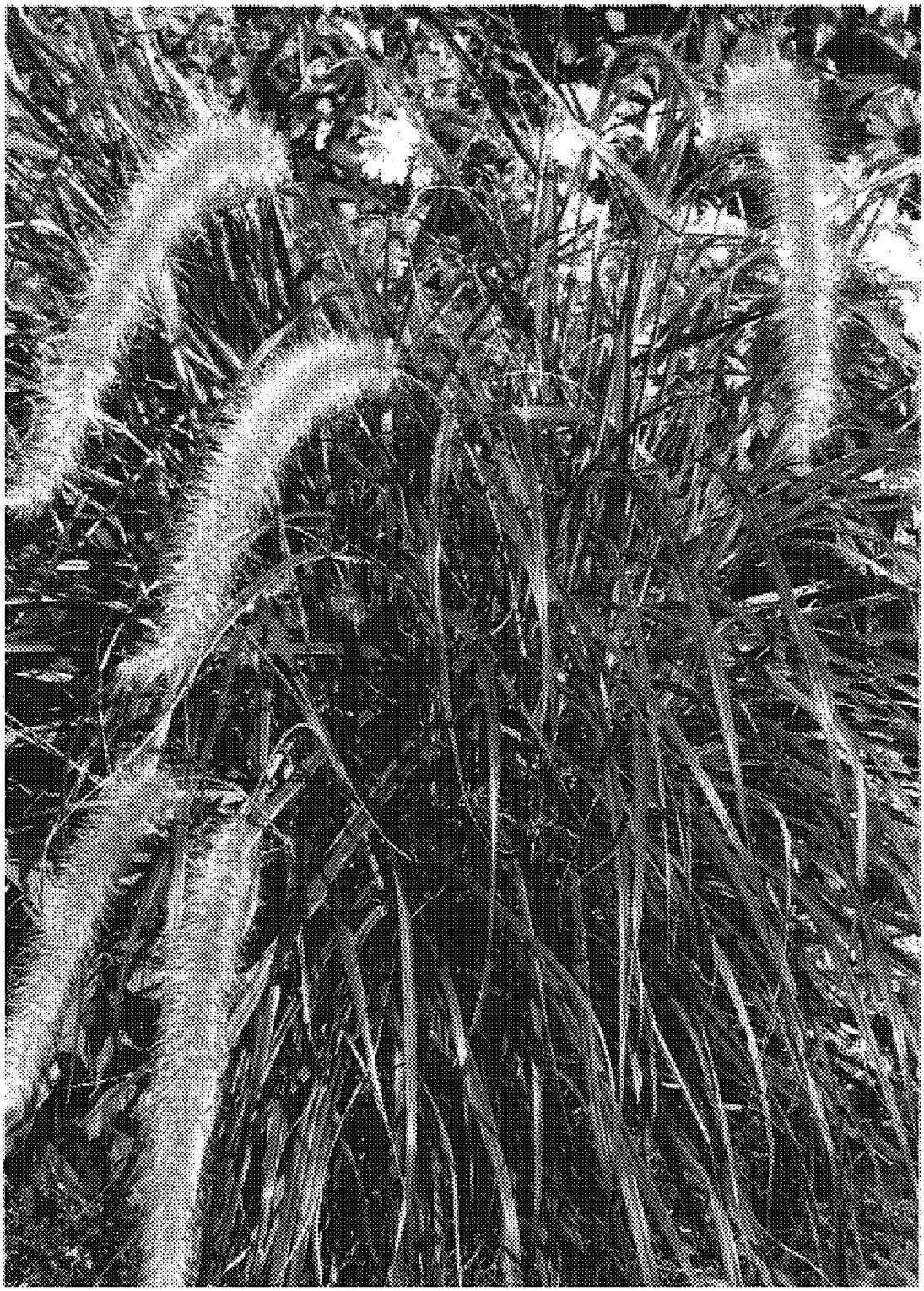
Figure 2:
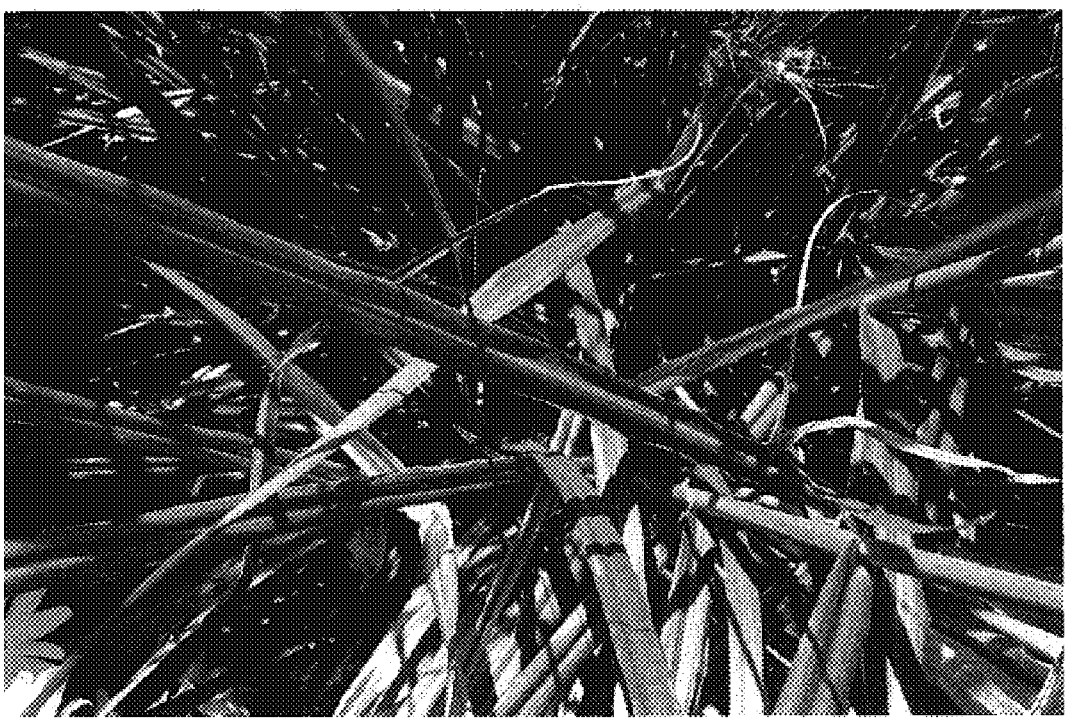

The photograph on FIG. 2 is a close-up view of the foliage coloration of 'Fireworks'.

The colors in the photographs are as close as possible with the photographic and printing technology utilized. The color values cited in the detailed botanical description accurately describe the colors of the new *Pennisetum.*

DETAILED BOTANICAL DESCRIPTION

The general observations and descriptions describe plants that are one year in age as grown outdoors in a two-gallon container. The color determinations are in accordance with the 2001 R.H.S. Colour Chart of The Royal Horticultural Society, London, England, except where general color terms of ordinary dictionary significance are used.

Botanical classification: 'Fireworks' is a cultivar of *Pennisetum setaceum.*
Common name: Fireworks Purple fountain grass.

Parentage: Culm sport of *Pennisetum setaceum* 'Rubrum'.

General description:

*Blooming period.*—Blooms from late June until frost in Leola, Pa.

*Plant habit.*—Herbaceous, clump-forming, ornamental grass with an upright culms and leaf blades that cascade in a vase-shaped form.

*Height and spread.*—Reaches a height of about 1.2 m (4 ft), and a spread of about 0.8 m.

*Cold hardiness.*—U.S.D.A. Zone 9, grown in colder climates as a seasonal grass.

*Culture.*—Grows best in fertile, well-drained soils in full sun, tolerant to wind but performs poorly in wet soils, foliage coloration is bet in full sun.

*Diseases and pests.*—*Pennisetum setaceum* and 'Fireworks' have no known disease resistance or pest problems.

*Root description.*—Fibrous.

Growth and propagation:

*Propagation.*—Culm division and tissue culture.

*Time required for root initiation.*—Roots appear in 7 to 10 days in a greenhouse grown under ambient light from February to September.

*Time required for root development from a single division.*—Roots will fully develop a 50-cell liner in 4 to 8 weeks depending on the time of year.

*Growth rate.*—Very vigorous, plants obtain mature height and flower in one growing season.

Culm (stem) description:

*General.*—Cylindrical, enclosed by leaf sheaths.

*Culm aspect.*—Held erect to slightly cascading.

*Culm color.*—144A to 144B and lightly suffused with 184B (comprised of leaf sheaths).

*Culm size.*—About 1 m in length and an average of 5 mm in width.

*Culm surface.*—Glabrous and slightly shiny.

*Internode length.*—Average of 5.5 cm.

Foliage description:

*Leaf shape.*—Linear.

*Leaf division.*—Simple.

*Leaf base.*—Sheathed.

*Leaf apex.*—Acute, tapering to a fine point.

*Leaf aspect.*—Emerging leaves are erect, leaf blades diverge from leaf sheath at ligule at up to a 20° C. to 40° angle from center of culm then gently cascading. Blades are flat to slightly concave and recessed at mid rib.

*Leaf venation.*—Parallel, mid rib is recessed on upper surface, color matches the color of the leaf blades on upper and lower surface.

*Leaf margins.*—Entire in appearance but finely scabrous to touch.

*Leaf persistence.*—Foliage dries but is persistent throughout the winter.

*Leaf attachment.*—Sheathed, leaf is sheathed from the base of culm and the blade extends out from the culm at a ligule.

*Ligule.*—Average of 1 mm in width, extends length of leaf blade, color is 144B in center and typically 183A near edges.

*Leaf size.*—Average of 32 cm in length and up to 1.2 cm in width; narrower at culm attachment and tapering to a point at the apex.

*Leaf surface.*—Glabrous on upper and lower surface with satin sheen.

*Leaf number.*—Average of 7 leaves per culm.

*Leaf arrangement.*—Alternate, 2 ranked.

*Leaf color and variegation pattern.*—Variegation is composed of vertical bands of burgundy, pink, green and white of varying widths. Variegation pattern and coloration occurs on upper and lower surface. Burgundy regions range from greyed-purple 187C to 187D, 186A to 186C and a blend of N186B and N186C, red purple 59C to purple N79C, green regions range are typically 147B and 137A to 137B to these colors blended with the purple tones, white stripes 155C, late summer and fall with cooler temperature the foliage becomes purpler 59C to N79C.

Flower description:

*General description.*—Inflorescence is a plumed raceme terminating from each culm, arching upward and then cascading, comprised of 1 to 2 spikelets surrounded by an involucre of bristles.

*Lastingness of inflorescence.*—Racemes dry but remain persistent.

*Fragrance.*—None.

*Panicle size.*—Range from 17 to 27 cm in length and an average of 3.5 cm in width.

*Panicle color.*—Emerge greyed-purple with (effectively 187C with apex blended with 196D due to bristles) and changes to a beige color with maturity (effectively 161C to 161D in color), rachis is about 1 mm in width with stripes of 144A and 144B.

*Spikelet description.*—Single or in groups of 2 to 3, average of 1.2 mm (2.5 cm including bristles) and 1.5 mm in width (3 mm including bristles), 2 glumes; membranous, transparent and suffused with 162C in color, one is minute and one is about 6 mm in length and 1.5 mm in width, palae; about 5 mm in length and 1.5 mm in length, lemma; translucent with slight tint of 162C, about 4 mm in length and 1 mm in width, bristles; attached to base of spikelet, up to 3.5 cm in length, unequal in length, plumose at base, 187B in color changing to 161D.

*Reproductive organs.*—Pistil; 1 with two plumose stigmas that are 6 mm in length, 0.4 mm in width and 187A in color, stamens; 2, shorter that stigmas, 1.3 mm in length, 0.3 mm in width and 144D in color, pollen; not visible.

*Seed.*—Seed set has not been observed, the parent plant, 'Rubrum', is known to rarely set seed.

I claim:

1. A new and distinct cultivar of *Pennisetum* plant named 'Fireworks' as herein illustrated and described.

* * * * *